(12) United States Patent
Lindeberg

(10) Patent No.: US 8,226,289 B2
(45) Date of Patent: Jul. 24, 2012

(54) MAGNETIC STIRRING SYSTEM IN A PVT CELL INCLUDING DRIVING SOLENOIDS AND A MONITORING SOLENOID

(75) Inventor: Erik Gøsta Bruno Lindeberg, Trondheim (NO)

(73) Assignee: Sinvent AS, Trondheim (NO)

( * ) Notice: Subject to any disclaimer, the term of this patent is extended or adjusted under 35 U.S.C. 154(b) by 622 days.

(21) Appl. No.: 11/991,178

(22) PCT Filed: Aug. 31, 2006

(86) PCT No.: PCT/NO2006/000308
§ 371 (c)(1),
(2), (4) Date: Aug. 27, 2009

(87) PCT Pub. No.: WO2007/027100
PCT Pub. Date: Mar. 8, 2007

(65) Prior Publication Data
US 2009/0323461 A1    Dec. 31, 2009

Related U.S. Application Data

(60) Provisional application No. 60/712,423, filed on Aug. 31, 2005.

(51) Int. Cl.
*B01F 13/08* (2006.01)
(52) U.S. Cl. .......................................... 366/142; 366/273
(58) Field of Classification Search ................... 366/129, 366/273, 274, 342, 343, 142; 99/277.2; 435/302.1; 416/3; 73/744
See application file for complete search history.

(56) References Cited

U.S. PATENT DOCUMENTS

| | | | |
|---|---|---|---|
| 6,007,227 A | 12/1999 | Carlson | |
| 6,065,865 A * | 5/2000 | Eyraud et al. | 366/273 |
| 6,455,316 B1 | 9/2002 | Turner et al. | |
| 6,688,180 B1 | 2/2004 | Lund et al. | |
| 6,834,990 B2 | 12/2004 | Nielsen | |
| 2009/0211364 A1* | 8/2009 | Lindeberg | 73/744 |
| 2009/0323461 A1* | 12/2009 | Lindeberg | 366/142 |

FOREIGN PATENT DOCUMENTS
CA    2 381 014    2/2000
WO    01/02089     1/2001

OTHER PUBLICATIONS

International Search Report mailed Dec. 20, 2006 for International Application No. PCT/NO06/000308.

* cited by examiner

*Primary Examiner* — Charles E Cooley
(74) *Attorney, Agent, or Firm* — Wenderoth, Lind & Ponack, L.L.P.

(57) ABSTRACT

A pVT cell for testing of fluids at high pressure includes a piston (1) and a stirring system for rapidly providing equilibrium prior to test measurement. The stirring system includes: an impeller (10) mounted for rotation on a shaft (11) in an impeller recess (2) on a fluid side of said piston (1), said impeller (10) including at least one permanent magnet; at least two driving solenoids (3) inside said piston (1) for influencing said at least one permanent magnet and thereby providing impeller (10) movement; and a monitoring solenoid (5) arranged inside said piston (1) close to but isolated from the impeller recess (2) in order to monitor the rotation of the impeller (10).

8 Claims, 1 Drawing Sheet

FIG. 1
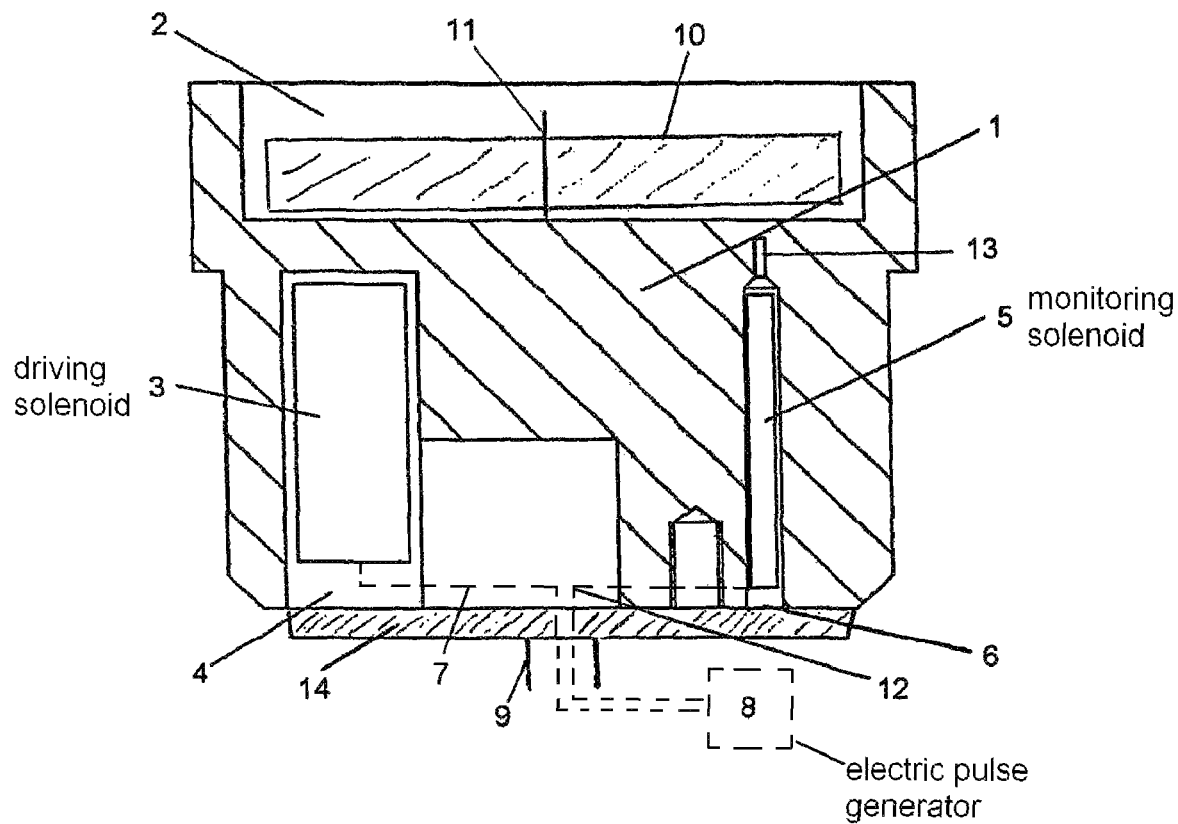
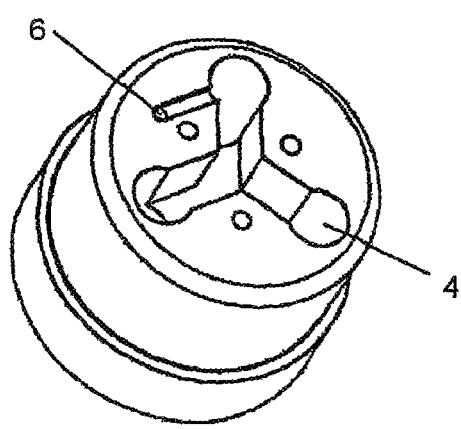
FIG. 2

MAGNETIC STIRRING SYSTEM IN A PVT CELL INCLUDING DRIVING SOLENOIDS AND A MONITORING SOLENOID

The present application hereby claims priority to U.S. Provisional Application No. 60/712,423, filed Aug. 31, 2005.

BACKGROUND OF THE INVENTION

1. Technical Field

The present invention relates to a system for stirring by a magnetic coupled impeller, for use in pressure, volume and temperature (pVT) studies, of reservoir fluids and their properties in the laboratory and in the field.

In pVT cells and condensate cells, petroleum fluids can be studied at varying pressure and temperature simulating the conditions in oil reservoirs before and during production. Typically these fluids contain gas. The change in fluid density (compressibility) and the tendency for the gas to come out of the solution at decreasing pressure are of particular interest.

pVT cells are optimized to study oils with dissolved gas, while condensate cells are optimized to study light oils with high gas to oil ratio. In the following description they are both referred to as pVT cells.

Until the late eighties, the method to control the pressure in these cells was to pump mercury in and out of the cells. Mercury was considered to be inert with the respect to the petroleum fluids. There were however some health risks involved in the handling of mercury at high pressure and temperature, and mercury pumping has to a large extent been replaced by other methods for changing the volume in pVT cells.

Several of the new designs are based on cylindrical cells with a sealed piston that can be moved by either direct mechanical drive or hydraulic drive.

By shaking the old pVT cells with mercury, the mercury would also provide good stirring, so that a fast equilibrium between the phases was obtained. Equilibrium is essential to achieve reliable and reproducible measurements. This feature is lost when the volume is controlled with a piston.

2. Description of Related Art

As described in more detail later, several pVT cells are equipped with a magnetically coupled stirrer for mixing of the fluids under test.

The principle of a loose magnetic pulse driven stirrer and placement/stirrer speed/stirrer drag in a high pressure cells is, among other places, described in Norwegian patent no. 312.921. While patent 312.921 is an optical method to detect viscosity changes, the present invention is suitable for any fluid where optical methods are not suitable.

The magnetic coupling between the solenoids and the stirrer is relatively weak, due to the geometry and because the magnetic field is supplied through the metal piston.

Some petroleum fluids are very viscous, and the stirrer may therefore not rotate at the desired frequency.

Some cells are not provided with a window, and it is therefore not possible to see the fluid (blind cells). In many cases it would not be possible to see the stirrer even if the cell has a window, because the fluids are so dark.

A monitoring device to indicate whether the impeller is stirring or not, is therefore needed to achieve assurance of reliable operation.

Several patents, e.g. U.S. Pat. No. 6,834,990, describe a shaft driven stirrer with various configurations, especially of the stirrer/impeller with the focus on providing special features, e.g. aeration with bubbles from air supplied through the shaft and high efficiency (low power) shear of the fluid etc.

The shaft driven stirrers are not magnetically coupled, but directly driven, with related sealing problems. The magnetic coupling provides a possibility of a closed container with long time pressure stability.

One patent, U.S. Pat. No. 6,007,227, describes a control system for a blender application. A control system typically involves a sensor for feedback of the controlled variable. However, in the present invention, the stirrer acceleration, speed or angular position is not a part of a control system.

An alternative apparatus from those described above is needed to perform pVT studies with a simple and reliable assurance of stirring and therefore mixing of fluids or phase equilibrium under test in cells without a means for visual observation of the fluid, or for fluids with high level of opacity in cells with means for visual observation. The alternative for monitoring should also be very compact with no moving parts.

BRIEF SUMMARY OF THE INVENTION

Hence, in accordance with the present invention there is provided a novel magnetic stirring system for providing equilibrium prior to test measurement in a high pressure pVT cell. More precisely, the present invention provides a pVT cell for testing of fluids at high pressure which includes a piston and a stirring system for rapidly providing equilibrium prior to test measurement. The stirring system includes: an impeller mounted for rotation on a shaft in an impeller recess on a fluid side of said piston, said impeller including at least one permanent magnet; at least two driving solenoids inside said piston for influencing said at least one permanent magnet and thereby providing impeller movement; and a monitoring solenoid arranged inside said piston close to but isolated from the impeller recess in order to monitor the rotation of the impeller.

The pVT cell may preferably be configured such that all solenoids are removably arranged in wells in a piston rear side opposite to said fluid side. The pVT cell may preferably be configured such that at least one of said monitoring solenoid and said driving solenoids is fitted with axially extended core toward said impeller recess, said extended core fitting in a well extension that permits a short minimum distance between said extended core and an impeller permanent magnet, thereby reducing stray magnetic fields. The pVT cell may preferably be configured such that said monitoring solenoid is connected by wiring to an external pulse indicator. The pVT cell may preferably be configured such that said driving solenoids are connected by wiring to an external pulse generator. The pVT cell may preferably be configured such that said impeller recess covers a substantial part of the fluid side area of the piston. The pVT cell may preferably be configured such that said impeller recess is cylindrical in shape with said shaft being arranged concentrically therein. The pVT cell may preferably further comprise a hollow rod fixed to a piston cover fastened to a piston rear side opposite said fluid side, said rod extending out of said cell, to provide a passage for wiring to and from said piston.

BRIEF DESCRIPTION OF THE DRAWINGS

In the following, a more detailed description will be given of illustrative embodiments of the present invention, and at the same time it will be referred to the appended drawings, in which:

FIG. 1 shows a cross section through a piston in accordance with one preferable embodiment of the invention; and FIG. 2 is a perspective view from the underside of the piston appearing in FIG. 1.

DETAILED DESCRIPTION OF THE INVENTION

One solution of assuring good stirring is to place a magnetic driven stirring impeller on top of the piston. An impeller 10 with inserted permanent magnets is placed on a shaft 11 in a cavity 2 on the test fluid side of the piston body 1.

The stirrer is energized by an assembly of solenoids 3 placed inside the piston 1 in separate wells 4 in the piston body, but separated from the fluids. One of these wells 4 is indicated in FIG. 1, while three such wells appear in FIG. 2.

The solenoids are placed parallel to the piston cylinder axis and with one end of the core pointing to the magnets in the impeller 10, while the opposite sides are magnetically connected to increase field strength and reduce stray fields.

The piston 1 must be made of a non-magnetic material, preferably an alloy (e.g. Hastelloy C, Inconel, 316 stainless steel etc.). Phased power pulses to the solenoids 3 are supplied by thin Teflon insulated electric wires 7 which are drawn through a hollow rod 9. The hollow rod 9 is mounted on a cover 14 closing the bottom of the piston 1. The wires 7 are connected to an electric pulse generator 8 on the outside of the cell. Rod 9 is attached in the centre of the piston 1, reaching out through the cell body through a dynamic seal, but is only shown as a very short stub in the schematic drawing of FIG. 1.

To be assured of operation of the stirrer, a small extra solenoid 5 with separate wires 12 is placed in its own well 6 in the piston, but isolated from the fluids so that the permanent magnet in the impeller 10 passes close to the tip (at ref. num. 13) of the solenoid 5 if it is rotating. This induces electric pulses strong enough that they can easily be separated from the induction due to the pulsing solenoids 3. An electronic pulse indicator 8 informs the operator of the status of the stirrer. (For simplicity, we have entered both the pulse indicator and the pulse generator in one common unit 8.)

In a practical embodiment, the pVT cell piston consists of two parts. One part is the main body 1 with a recess 2 for an impeller 10 and fixing shaft 11 on the fluid-under-test side, an outer section with reduced diameter for piston-cylinder seals and guides, and wells 4, 6 for solenoids 3, 5 and wires 7, 12 extending from the other side. The other part is a cover 14 with a piston rod 9 attached. Between and in the cover 14 and the main body, there are seals so that the inside of the piston is sealed off from both hydraulic fluid and the fluid under test. (In FIG. 2, the cover 14 has been left out to show wells 4, 6.)

The stirring impeller 10, that can rotate freely on the shaft 11 in the piston recess 2, has preferably a symmetrical design and has two or more symmetrically located permanent magnets.

The stirring operation is performed by energizing the two or more driving solenoids 3 sequentially, thereby pushing and pulling the impeller permanent magnets. The driving solenoids 3 are designed as a magnetically soft core with cylindrically wound wire. The number of windings and wire thickness and material may vary with desired magnetic force and other features. The driving solenoids 3 can be arranged axially inside the piston 1 or radially outside the cylinder, resembling an ordinary electric motor or step motor.

In most embodiments, the impeller is fixed axially on the shaft and can only rotate about the shaft axis. The shaft can be designed as a detachable unit either in the form of a single screw entered from the piston top, or a disk with an extended shaft. The shaft can also be an integral part of the piston. The rotation of the impeller mixes and stirs the fluids under test.

The monitoring of the stirring is performed by having a solenoid 5 with separate wires 12 in a separate well 6 inside the piston 1. The wires 7, 12 can also be connected in such a way as to form a common reference for the driving and monitoring solenoids 3, 5.

The monitoring solenoid 5 gives pulses caused by induction from the passing permanent magnets in the rotating impeller 10.

The cavity or well 6 for the monitoring solenoid 5 is shown with space 13 for an extended core, while the well 4 for the driving solenoid 3 is shown without.

While the foregoing preferred embodiments of the invention have been described and shown, it is understood that all alternatives and modifications, such as those suggested and other, may be made thereto and follow the scope of the invention.

The invention claimed is:

1. A pVT cell for testing of fluids at high pressure including a piston (1) and a stirring system for rapidly providing equilibrium prior to test measurement, said stirring system comprising:
   an impeller (10) mounted for rotation on a shaft (11) in an impeller recess (2) on a fluid side of said piston (1), said impeller (10) including at least one permanent magnet;
   at least two driving solenoids (3) inside said piston (1), for influencing said at least one permanent magnet and thereby providing impeller (10) movement; and
   a monitoring solenoid (5) arranged inside said piston (1) close to but isolated from the impeller recess (2), in order to monitor the rotation of the impeller (10).

2. The pVT cell of claim 1, wherein all solenoids (3, 5) are removably arranged in wells (4, 6) in a piston rear side opposite to said fluid side.

3. The pVT cell of claim 2, wherein at least one of said monitoring solenoid (5) and said driving solenoids (3) is fitted with axially extended core toward said impeller recess (2), said extended core fitting in a well extension (13) that permits a short minimum distance between said extended core and an impeller permanent magnet, thereby reducing stray magnetic fields.

4. The pVT cell of claim 1, wherein said monitoring solenoid (5) is connected by wiring (12) to an external pulse indicator (8).

5. The pVT cell of claim 1, wherein said driving solenoids (3) are connected by wiring (7) to an external pulse generator (8).

6. The pVT cell of claim 1, wherein said impeller recess (2) covers a substantial part of the fluid side area of the piston (1).

7. The pVT cell of claim 1, wherein said impeller recess (2) is cylindrical in shape, said shaft (11) being arranged concentrically therein.

8. The pVT cell of claim 1, further comprising a hollow rod (9) fixed to a piston cover (14) fastened to a piston rear side opposite said fluid side, said rod (9) extending out of said cell, to provide a passage for wiring (7, 12) to and from said piston (1).

* * * * *